United States Patent [19]

Beroff

[11] 4,230,110
[45] Oct. 28, 1980

[54] HUB WITH SUTURING PROVISION FOR MEDICAL DEVICES

[75] Inventor: Howard Beroff, Bridgewater, N.J.

[73] Assignee: Johnson & Johnson, New Brunswick, N.J.

[21] Appl. No.: 935,840

[22] Filed: Aug. 22, 1978

[51] Int. Cl.³ ............................................. A61M 5/00
[52] U.S. Cl. ................................... 128/214.4; 128/348
[58] Field of Search ............... 128/214 R, 214.4, 221, 128/348–351; 27/24 A

[56] References Cited

U.S. PATENT DOCUMENTS

| 1,109,626 | 9/1914 | Davis | 128/221 X |
|---|---|---|---|
| 3,176,690 | 4/1965 | H'Doubler | 128/348 |
| 3,219,036 | 11/1965 | Stafford | 128/214.4 |
| 3,777,761 | 12/1973 | Sheridan | 128/350 R |
| 3,825,001 | 7/1974 | Bennet et al. | 128/214.4 |
| 4,046,144 | 9/1977 | McFarlane | 128/214.4 |
| 4,122,858 | 10/1978 | Schiff | 128/348 |

FOREIGN PATENT DOCUMENTS 1534119  6/1968  France ................................ 128/214.4

*Primary Examiner*—Dalton L. Truluck
*Attorney, Agent, or Firm*—Donal B. Tobin

[57] ABSTRACT

A hub device particularly suitable for use in a catheter placement unit which includes a catheter tube for insertion into a patient. The hub comprises a body with a passageway therethrough for the passage of the catheter tube, and includes a thin-walled, pierceable annular flange integrally formed on one end of the body. This flange is adapted to be pierced for suturing the hub to a patient and thereby anchor the same in place.

1 Claim, 5 Drawing Figures

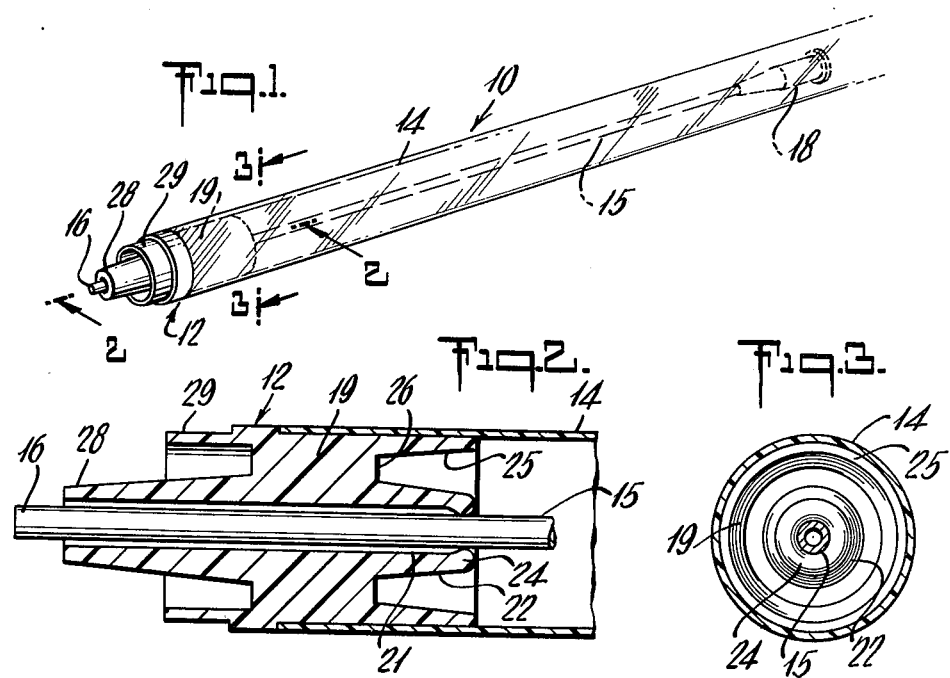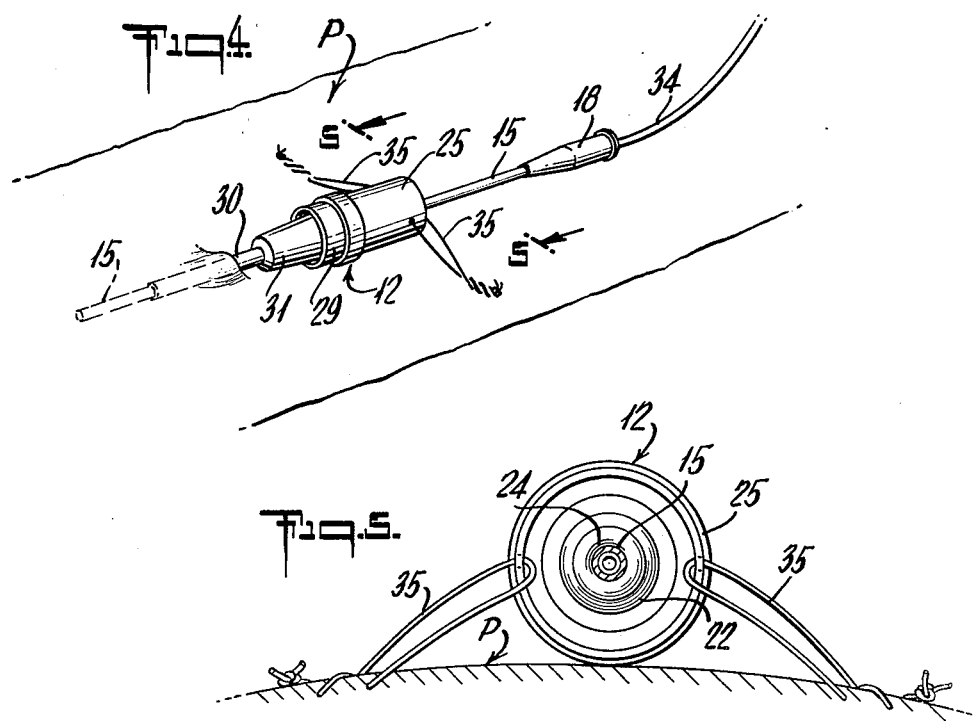

HUB WITH SUTURING PROVISION FOR MEDICAL DEVICES

BACKGROUND OF THE INVENTION

The present invention relates to a hub suitable for use with medical devices which are to remain in a fixed position on a patient, and more particularly, concerns a hub suitable for use in a catheter placement unit in which the hub is sutured to the patient to anchor the same in place.

Catheter placement units are employed for a variety of purposes, including the administration of liquids into the blood stream, monitoring the central venous pressure and the like. Extended catheter tubes are embodied within such a catheter placement unit so that the tube may be positioned far into a remote position within the patient. Once the tip of the catheter tube reaches the appropriate location within the body, for example at the right atrium of the heart, it is desirable to fix the placement unit in place so that it can no longer move. In many well-known catheter placement units, a piece of thin shrinkable tubing is located around the outside surface of the placement unit hub. One technique for fixing the placement unit in position after the catheter tube is properly located has been to pass a needle and suture through the skin of the patient and then through the piece of shrinkable tubing around the hub. While such a technique serves the function intended, the stability of the sutured shrinkable tubing is oftentimes less than desirable. For instance, the shrinkable tubing itself may loosen thereby allowing some relative movement between the shrinkable tubing and the hub. Furthermore, the addition of a piece of shrinkable tubing around the hub is an extra manufacturing operation which not only adds time and expense to the operation, but also includes an extra structural element which must be inspected for quality assurance purposes. Accordingly, improvements in fixing medical devices such as catheter placement units in position on a patient are still being sought, and it is to this end that the present invention is directed.

SUMMARY OF THE INVENTION

A hub of the present invention is suitable for use with medical devices which are to remain in a fixed position on a patient. Comprising this hub is a body with a passageway therethrough adapted to receive a tubular member for insertion into a patient. A thin-walled pierceable section is integrally formed on the body and is adapted to be pierced for suturing the hub to the patient and thereby anchor the same in place.

In the preferred embodiment of this aspect of the present invention, the thin-walled section is an annular flange integrally formed on one end of the body, both the body and the flange being a unitary structure formed of elastomeric material.

Another aspect of the present invention is a catheter placement unit including a hub, a protective sleeve connected to the hub and a catheter tube within the sleeve adapted to pass through the hub for insertion into a patient. Comprising the hub is a body with a passageway therethrough for the passage of the catheter tube, and also a thin-walled pierceable section integrally formed on the body adapted to be pierced for suturing the hub to the patient.

A significant advantage of the present invention is that the pierceable section which provides the suturing provision is directly connected to the body of the hub. There can be no loosening of this suturing section as is often possible when shrinkable tubing is used around the hub in the previously known catheter placement units as discussed above. Another advantage is the economic fabrication of such a hub inasmuch as the unitary hub with the suturing section may be molded out of elastomeric material thereby providing a readily pierceable suturing section. In addition, when using an elastomeric material which is generally resilient, the hub of the present invention may incorporate other features such as sealing elements associated with the passageway of the hub. Inclusion of a sealing element on the hub device is desirable to prevent leakage of liquid out of the hub when, for instance, a catheter tube extends through the hub and is inserted in a patient. These advantages are a result of the structural formation of the hub of the present invention.

BRIEF DESCRIPTION OF THE DRAWINGS

FIG. 1 is a perspective view illustrating one embodiment of a catheter placement unit including a preferred hub of the present invention;

FIG. 2 is an enlarged cross-sectional view taken along line 2—2 of FIG. 1;

FIG. 3 is an enlarged cross-sectional view taken along line 3—3 of FIG. 1;

FIG. 4 is a view showing the catheter placement unit inserted into a patient with the hub being sutured to the patient to hold the same in place; and FIG. 5 is an enlarged cross-sectional view taken along line 5—5 of FIG. 4.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principals of the invention and is not intended to limit the invention to the embodiment illustrated. The scope of the invention will be pointed out in the appended claims.

Adverting to the drawings, particularly to FIG. 1, there is illustrated a catheter placement unit 10 which is utilized to deliver a catheter especially to a remote part of the human body. Catheter placement unit 10 is comprised of a hub 12, a protective sleeve 14 connected at one end to hub 12 and a catheter tube 15 within sleeve 14, the tube adapted to pass through hub 12, for eventual insertion into a patient. A distal end 16 of tube 15 is normally inserted in hub 12 so as to project a short distance from the hub thereby placing a catheter placement unit in a better state of readiness for utilization. At the proximal end of catheter tube 15 is a fitting 18 through which appropriate tubing from an administration set or a pressure monitoring device is connected after the catheter tube has been positioned. Sleeve 14 is preferably very pliant or flexible, and removable from the catheter placement unit after catheter tube 15 has been positioned in the patient.

Turning to FIGS. 2 and 3, hub 12 is more clearly illustrated. As can be seen in the drawings, hub 12 includes a generally cylindrically shaped body 19. On the periphery of body 19 is an annular shoulder 20 against which sleeve 14 lies and which assists in the connection of sleeve 14 to hub 12. A substantially circular passageway 21 extends through the longitudinal direction of body 19. One end of body 19 includes a tapered annular projection 22 around passageway 21. At the end of projection 22 is an annular dimple 24, the diameter of the dimple being less than the diameter of the passageway. As can be seen especially in FIG. 2, tube 15 has been inserted into passageway 21 of the hub. Tapered projection 22 is designed to resiliently flex generally in a radially outward direction under the influence of catheter tube 15 being inserted through the circular opening formed by annular dimple 24. Both the relatively thin wall of the tapered projection and the fact that the body material itself is preferably flexible contribute to the resiliency of the tapered projection and allow the catheter tube to be slid relatively easily into passageway 21. At the same time, however, annular dimple 24 bears against the periphery of catheter tube 15 to thereby form a seal between annular dimple 24 and tube 15. This seal serves to prevent blood or other body fluids which may enter passageway 21 during use from leaking out of the hub. This seal is especially effective when body 19 and projection 22 are made of a flexible, preferably elastomeric, material.

Surrounding projection 22 and extending from one end of body 19 is an annular flange 25. This flange is integrally formed on the body of the hub so that the body and the flange are unitary in structure. Annular flange 25 is essentially a thin-walled pierceable section of material adapted to be pierced by, for example, a needle for suturing the hub to a patient to thereby anchor the hub in position. As seen in FIGS. 2 and 3 there is a spacing 26 between projection 22 and annular flange 25 which allows a needle to pierce the flange and be manipulated through spacing 26 in order to allow the suture to pull tightly and afford the proper fixation of the hub in position. The preferable material used for the unitary body and flange is an elastomeric material, such as natural rubber, synthetic rubber and the like, which readily lends itself to be pierced by a sharp instrument such as a needle.

At the opposite end of body 19 is a second tapered portion 28 serving as a male connector as will hereinafter be described. Tapered male connector 28 is preferably integrally formed on body 19 and extends substantially axially therefrom and is substantially concentric with passageway 21. It is noted that a distal end 16 of the catheter tube extends a short distance from the end of tapered male portion 28; this is to assure that the catheter tube has been properly inserted into passageway 21 so that the operator of the catheter placement unit does not have to make such insertion while he is trying to connect the catheter placement unit to an introducer catheter already inserted in the patient. Surrounding tapered male portion 25 is an annular rim 29 which, together with tapered male portion 28, serves to lock the hub into a compatible female fitting on the introducer catheter which is used in conjunction with the catheter placement unit for inserting the catheter tube into a patient. Although not shown for clarity sake, rim 29 may have threads or notches therein in order to provide a liquid-tight lock between hub 12 and the introducer catheter so that no blood or other body liquids may leak from the connection. Such an arrangement is more clearly seen in FIGS. 4 and 5, which also illustrate the use of the catheter placement unit and the advantageous features of the preferred hub of the present invention.

As can be seen in FIGS. 4 and 5, an introducer catheter 30 has been inserted into a patient P. At the proximal end of introducer catheter 30 is a fitting 31 with an internal tapered surface which serves as a female connector. A protruding border (not shown) on fitting 31 assists in locking the hub of the catheter placement unit to the introducer catheter. The connection of the catheter placement unit is made by the insertion of tapered male portion 28 into fitting 31, with rim 29 on the hub and the border on the fitting cooperating to provide a liquid-tight lock. Catheter tube 15 is then manipulated into introducer catheter 30 and then into the patient until the tip of the catheter tube reaches the desired location. Once catheter tube 15 is properly positioned, the protective sleeve is generally removed from hub 12 and a connection, such as tubing 34 from an administration set or pressure monitoring device, is made to fitting 18 at the proximal end of tubing 15. In this condition, the catheter placement unit is functionally operable to perform the intended purpose. However, in order to assure that the catheter placement unit does not move after the catheter tube has been properly located, one technique is to suture the hub of the placement unit directly to the patient. This suturing technique is illustrated in FIGS. 4 and 5.

A section of suitable suture material 35 is connected to a needle in the well-known fashion; the point of the needle is passed through thin-walled flange 25 and then stitched to the patient P in the normal manner. Suturing the hub on two opposite sides thereof to the patient serves to provide better balance and stability in the affixation technique. By suturing the hub to the patient, the catheter placement unit is anchored in position to prevent or at least minimize any movement of the unit during its use.

Thus, the present invention provides a hub which is especially suitable for use in medical devices which are to remain in a fixed position on a patient.

What is claimed is:

1. A hub suitable for use with an introducer catheter and adapted to remain in a fixed position on a patient comprising:

a body with a passage therethrough adapted to receive a catheter for insertion into a patient and having a diameter greater than the outer wall of said catheter to facilitate the easy insertion of said catheter therethrough without substantial frictional resistance;

a first thin walled flange extending from said body, coaxially aligned about said passageway and defining an extension thereof coterminous therewith;

an annular dimple on the end of said first flange and projecting into said passage extension and engaging the outer periphery of said catheter and providing a resilient seal thereagainst but permitting said catheter to slide therethrough into said passageway;

a second thin walled flange extending from said body and coaxially aligned with the axis of said passageway and having an interior wall spaced radially apart from said first thin walled flange, said second thin walled flange including a pierceable section adapted to be pierced for suturing said hub to said patient and thereby anchoring the same in place regardless of the angular orientation of said hub with respect to the patient, said radial space between said first and said second flanges permitting the passage of a suture needle.

* * * * *